(12) United States Patent
Bocks et al.

(10) Patent No.: US 12,337,081 B2
(45) Date of Patent: Jun. 24, 2025

(54) BIORESORBABLE ENDOLUMINAL PROSTHESIS FOR MEDIUM AND LARGE VESSELS

(71) Applicants: CASE WESTERN RESERVE UNIVERSITY, Cleveland, OH (US); MICHIGAN TECHNOLOGICAL UNIVERSITY, Houghton, MI (US)

(72) Inventors: Martin Bocks, Shaker Heights, OH (US); Jaroslaw Drelich, Houghton, MI (US); Jeremy Goldman, Hougton, MI (US); Ehsan Mostaed, Hougton, MI (US)

(73) Assignees: CASE WESTERN RESERVE UNIVERSITY, Cleveland, OH (US); MICHIGAN TECHNOLOGICAL UNIVERSITY, Houghton, MI (US)

( * ) Notice: Subject to any disclaimer, the term of this patent is extended or adjusted under 35 U.S.C. 154(b) by 911 days.

(21) Appl. No.: 17/402,513

(22) Filed: Aug. 14, 2021

(65) Prior Publication Data
US 2022/0047781 A1 Feb. 17, 2022

Related U.S. Application Data

(60) Provisional application No. 63/065,842, filed on Aug. 14, 2020.

(51) Int. Cl.
*A61F 2/02* (2006.01)
*A61F 2/82* (2013.01)
(Continued)

(52) U.S. Cl.
CPC .............. *A61L 31/022* (2013.01); *A61F 2/82* (2013.01); *A61L 31/148* (2013.01);
(Continued)

(58) Field of Classification Search
CPC .................................. A61L 31/148; A61F 2/82
See application file for complete search history.

(56) References Cited

U.S. PATENT DOCUMENTS

| 6,287,332 B1 | 9/2001 | Bolz et al. |
| 7,651,527 B2 | 1/2010 | Krivoruchko et al. |
| | (Continued) | |

FOREIGN PATENT DOCUMENTS

WO WO-2020028643 A1 * 2/2020 ........... A61L 27/427

OTHER PUBLICATIONS

CN 109939271 A and translation thereof. (Year: 2024).*
CN 105925847 A and translation thereof (Year: 2024).*
CN 107519539 A and translation thereof (Year: 2024).*

*Primary Examiner* — Rebecca S Preston
(74) *Attorney, Agent, or Firm* — Tarolli, Sundheim, Covell & Tummino LLP

(57) ABSTRACT

An endoluminal prosthesis includes an implantable scaffold and/or stent substrate which is convertible from a compressed first geometric shape to a radially dilated dimensionally stable second tubular second geometric shape, the scaffold and/or stent substrate comprising a bioresorbable zinc alloy, the zinc alloy including at least at least four alloying elements selected from the group consisting of silver (Ag) in an amount of about 1.0 wt. % to about 6.0 wt. %, manganese (Mn) in an amount of about 0.1 wt. to about 2.0 wt. %, zirconium (Zr) in an amount of about 0.05 wt. % to about 1.0 wt. %, copper (Cu) in an amount of about 0.5 wt. % to about 1.2 wt. %, and optionally titanium (Ti) in an amount of 0 to about 0.4 wt. %, with the balance of the alloy being zinc and incidental impurities.

18 Claims, 1 Drawing Sheet

(51) Int. Cl.
    *A61L 31/02*     (2006.01)
    *A61L 31/14*     (2006.01)
    *A61L 31/08*     (2006.01)
    *A61L 31/16*     (2006.01)

(52) U.S. Cl.
    CPC . *A61F 2210/0004* (2013.01); *A61F 2240/001* (2013.01); *A61F 2250/001* (2013.01); *A61F 2250/0059* (2013.01); *A61F 2250/0067* (2013.01); *A61F 2250/0082* (2013.01); *A61L 31/08* (2013.01); *A61L 31/16* (2013.01)

(56) References Cited

U.S. PATENT DOCUMENTS

| | | |
|---|---|---|
| 10,660,772 B2 | 5/2020 | Schwartz et al. |
| 10,898,355 B2 | 1/2021 | Hehrlein |
| 2009/0306765 A1* | 12/2009 | Weber .................. A61L 31/022 |
| | | 427/2.25 |
| 2014/0200652 A1* | 7/2014 | Bayer ...................... C23G 1/12 |
| | | 420/407 |
| 2018/0133040 A1 | 5/2018 | Stankus et al. |
| 2019/0032173 A1* | 1/2019 | Sherman ............. C22C 32/0073 |
| 2020/0253757 A1* | 8/2020 | Sirhan .................... A61F 2/915 |

\* cited by examiner

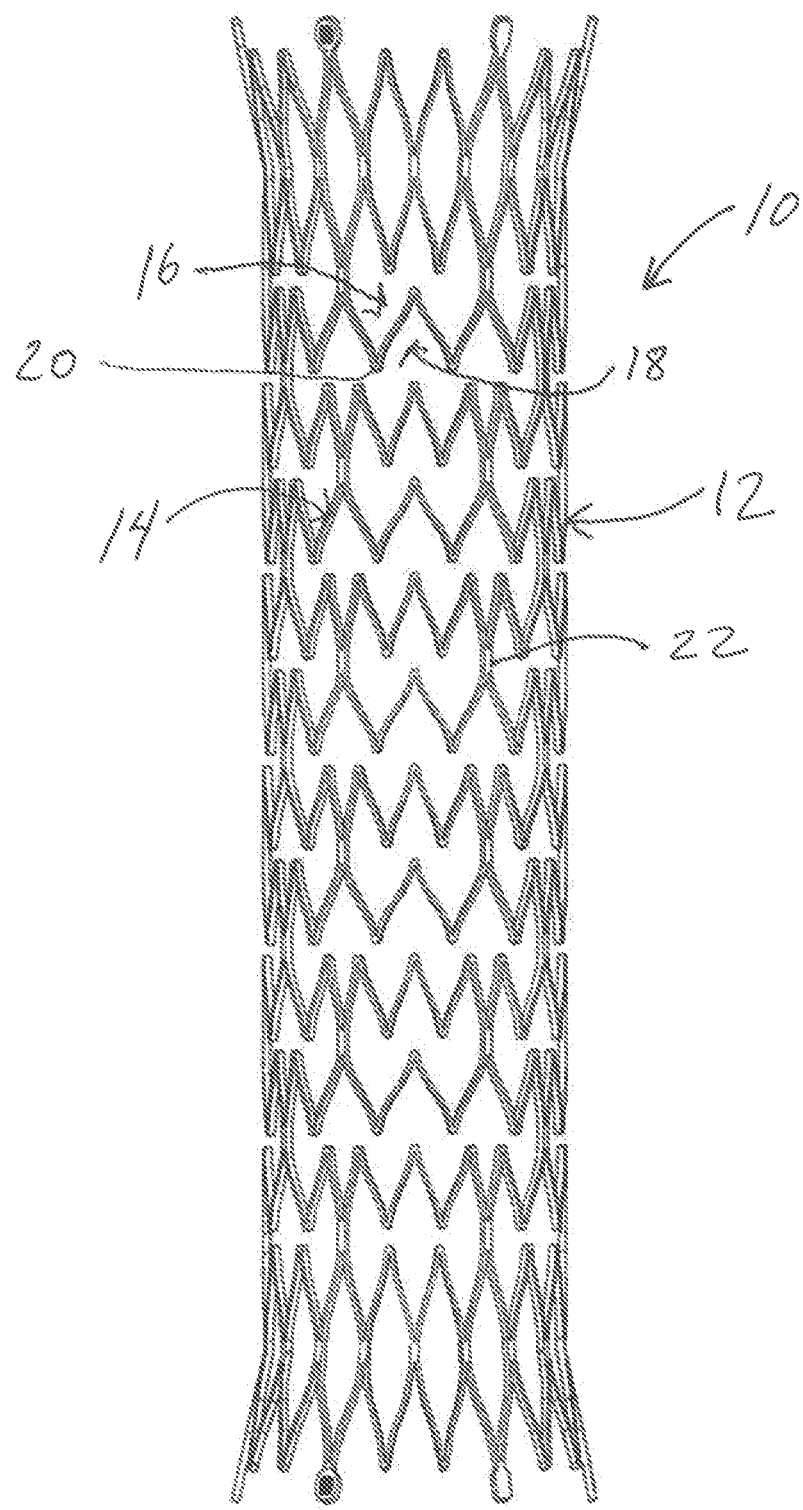

BIORESORBABLE ENDOLUMINAL PROSTHESIS FOR MEDIUM AND LARGE VESSELS

RELATED APPLICATION

This application claims priority from U.S. Provisional Application No. 63/065,842, filed Aug. 14, 2020, the subject matter of which is incorporated herein by reference in its entirety.

GOVERNMENT FUNDING

This invention was made with government support under grant HL144739 awarded by the National Institutes of Health. The government has certain rights in the invention.

BACKGROUND

Numerous pediatric congenital heart diseases and acquired adult vascular diseases are characterized pathognomonically by the narrowing of blood vessels, including both arteries and veins, that are vital to sustain life or to allow a particular organ system to function normally. In infants, children, and young adults, the vascular stenoses are often treated by the placement of a bare metal stent (BMS). However, when a BMS is placed in a child that is still growing, that portion of the vessel will no longer grow. The younger the patient, the more growth restricting a vascular stent can be, and many of these stents cannot be dilated to an adult size making BMS a poor option for many pediatric patients.

In adults, various acquired conditions can develop including coronary artery disease, peripheral and carotid vascular disease, in which vascular stenoses develop leading to stroke, heart attacks, and loss of limbs. In these conditions endovascular stenting with BMS is a commonly utilized treatment. Use of these commercially available permanent BMSs allows for initial treatment of the vascular stenosis, but long term presence of the stent material can lead to late thrombus formation, inflammation, and ongoing in-stent restenosis from cumulative neointimal hyperplasia.

Recently, zinc (Zn) based materials have been introduced as a new class of absorbable biometals for stent applications. Zn has been alloyed with metals, such as Mg and Al, to improve the mechanical properties of zinc for use as a stent material. Zn—Mg alloys, however, have shown little promise due to a decreased elongation to failure after hot extrusion compared to pure Zn. Zn—Al alloys have shown low-strengths and a lack of work hardening making use of these material challenging for endovascular stents.

Much focus of bioresorbable stent has been on adult coronary artery disease use, in which the maximum achievable diameter to date is 3.0 mm. There is a tremendous need for bioresorbable stents to achieve larger diameters for certain pediatric and adult conditions.

SUMMARY

Embodiments described herein relate to an endoluminal prosthesis that includes an implantable scaffold and/or stent substrate, which is convertible from a compressed first tubular geometric shape to a radially expanded or dilated dimensionally stable second tubular geometric shape. The scaffold and/or stent material includes a bioresorbable zinc alloy that provides optimal tensile strength while maintaining ductility and elongation to failure characteristics to allow the stent substrate to be radially expanded from a first geometric shape capable of fitting in a 1 to 2 mm delivery sheath to a second geometric shape having an outer diameter of, for example, about 4 mm to about 12 mm. Advantageously, the implantable stent material, which is radially expandable from about 4 mm to about 12 mm and which is formed using the bioresorbable zinc alloy described herein, can be used in pediatric and adult conditions in which large bioresorbable stents are beneficial. Such conditions can include, for example, infant/pediatric pulmonary artery stenosis (e.g., about 4 to about 12 mm), infant/pediatric aortic coarctation (e.g., about 4 to about 12 mm), neonatal patent ductus arteriosus stenting (e.g., about 6 to about 8 mm), infant RVOT stenting (e.g., about 4 to about 8 mm), pulmonary vein stenosis/occlusion (e.g., about 4 to about 10 mm), adult peripheral artery disease (about 4 to about 12 mm), adult coronary artery disease (e.g., about 4 to about 5 mm), adult carotid artery disease (e.g., about 6 to about 10 mm), adult renal artery stenosis (e.g., about 4 to about 10 mm), and adult and children venous and arterial thrombosis recanalization (e.g., about 4 to about 12 mm).

In some embodiments, the bioresorbable zinc alloy includes at least four alloying elements selected from the group consisting of Ag in an amount of about 1.0 wt. % to about 6.0 wt. %, Mn in an amount of about 0.1 wt. to about 2.0 wt. %, Zr in an amount of about 0.05 wt. % to about 1.0 wt. %, Cu in an amount of about 0.5 wt. % to about 1.2 wt. %, and optionally Ti in an amount of 0 to about 0.4 wt. %, with the balance of the alloy being zinc and incidental impurities.

Advantageously, the bioresorbable zinc alloy used to form the implantable stent substrate can have an ultimate tensile strength of greater than about 250 MPa and/or an elongation to fatigue greater than about 25%, which can allow for therapeutic maintenance of vessel patency at the target size and the implantable stent to be delivered through small introducer sheaths. In some embodiments, the implantable stent substrate can have a radial strength of at least about 2 N/mm at an outer diameter of about 6 mm and a radial strength of at least about 0.9 N/mm at an outer diameter of 10 mm.

In some embodiments, the bioresorbable zinc alloy can have a substantially uniform microstructure with a Zn grain size of about 0.1 μm to about 10 μm and a plurality of uniformly distributed intermetallic particles at the grain boundaries. The intermetallic particles can have a size of about 100 nm to about 1 μm.

In some embodiments, the implantable stent substrate after implantation in vasculature of a subject in need thereof, can maintain ductility after exposure to vascular pulsability and during degradation as well as maintain vessel patency at least 6 months.

The bioresorbable zinc alloy can be cast at a temperature of about 650° C. and extruded at a temperature in the range of about 250° C. to about 300° C. and at an extrusion ratio of about 8:1 to about 40:1.

The endoluminal prosthesis can also include a coating on the implantable stent substrate. In some embodiments, the coating can prevent or delay degradation of the implantable bioresorbable stent substrate. In other embodiments, the coating can hold or release at least one therapeutic agent after implantation of the endoluminal prosthesis and/or over a sustained duration of time after implantation.

BRIEF DESCRIPTION OF THE DRAWINGS

FIG. 1 is a schematic illustration of stent in accordance with an embodiment described herein.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "or" as used herein should be understood to mean "and/or", unless the context clearly indicates otherwise.

The term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

All percentages and ratios used herein, unless otherwise indicated, are by weight.

Embodiments described herein relate to an endoluminal prosthesis that includes an implantable bioresorbable scaffold and/or stent substrate, which is convertible from a compressed first tubular geometric shape to a radially expanded or dilated dimensionally stable second tubular geometric shape. The scaffold and/or stent substrate includes a bioresorbable zinc alloy that provides optimal tensile strength while maintaining ductility and elongation to failure characteristics to allow the stent substrate to be radially expanded from a first geometric shape capable of fitting in a 1 to 2 mm delivery sheath to a second geometric shape having an outer diameter of, for example, about 4 mm to about 12 mm. Advantageously, an implantable scaffold and/or stent substrate, which is radially expandable to about 4 mm to about 12 mm and which is formed using the bioresorbable zinc alloy described herein, can be used in pediatric and adult conditions in which large bioresorbable scaffolds and/or stents are beneficial.

In some embodiments, the manufacturing process and zinc alloy compositions described herein represent a new use of a zinc biomaterial and a manufacturing process. The method of heating and annealing the zinc alloys described herein optimizes the tensile strength of the zinc alloy without creating mechanical stress cracks or fractures before laser cutting. Thus, the zinc alloy allows for the creation of a scaffold and/or stent with a desired wall thickness of about 80 to about 160 micrometer and thus allows for a small enough crossing profile to be used in even the smallest of patients.

In some embodiments, the scaffold and/or stent material described herein can have excellent elongation to fatigue characteristics (>25%) and tensile strength (>250 MPa) allowing for therapeutic maintenance of vessel patency at the target size while allowing the scaffold and/or stent material to be delivered through small introducer sheaths. Fine and uniformly dispersed metallic particles formed during in the zinc alloys during the manufacturing process is the reason these stent characteristics can be achieved and is what can separate the scaffold and/or stent described herein from prior art stents which only have a practical application for treating much smaller target lesions.

Moreover, we found that the zinc alloy wires when placed intravascularly result in the production and release of $Zn^{2+}$, which induces neointimal smooth muscle cell (SMC) apoptosis without decreasing the presence of endothelial cells. Lower numbers and decreased activity of SMC near the stent is one of the mechanisms postulated for the reduction in the NIH response. Furthermore, the zinc alloys described herein that include copper can release $Cu^{2+}$ during degradation, which regulates endothelial response and the upregulation of nitric oxide (NO) production. Local NO production can have a profound effect on reducing platelet activation, improving vasomotor function, and inhibiting NIH. Thus, the zinc alloys described herein have anti-inflammatory and NIH inhibitory effects without the requirement the addition of an antiproliferative agent. This property is another distinct advantage of the zinc alloys described herein especially for the pediatric applications and adults with atherosclerotic disease when combined with the other properties above.

FIG. 1 illustrates an example of an implantable stent substrate 100 of an endoluminal prosthesis. Stent substrate 100 is a patterned tubular device that includes a plurality of radially expandable cylindrical rings 12. Cylindrical rings 12 are formed from struts 14 provided in a generally sinusoidal pattern including peaks 16, valleys 18, and segments 20 connecting peaks 16 and valleys 18. Connecting links 22 connect adjacent cylindrical rings 12 together. In FIG. 1, connecting links 22 are shown as generally connecting peak 16 of one ring 12 to valley 18 of an adjacent ring 12. However, connecting links 22 may connect a peak 16 of one ring 12 to a peak 16 of an adjacent ring, or a valley 18 to a valley 18, or a straight segment 20 to a straight segment 20. Further, connecting links 22 may be straight or curved. Connecting links 22 may also be excluded, with a peak 16 of one ring 12 being directly attached to a valley 18 of an adjacent ring 12, such as by welding, soldering, or the manner in which stent 100 is formed.

It will be appreciated by those of ordinary skill in the art that the stent substrate 100 pattern of FIG. 1 is merely an exemplary stent substrate pattern and that the stent described herein can have other stent substrate patterns. Examples of other stent scaffold patterns are disclosed in U.S. Patent Application Publication Nos. 2008/0275537, 2010/0004735, 2011/0190871, 2011/0190872, 2018/0133040, and 2018/0042740 all of which are incorporated by reference in their entirety.

The implantable stent substrate 100 can be made partially or completely from a biodegradable, bioresorbable, and bioabsorbable zinc alloy. The terms biodegradable, bioresorbable, bioabsorbable, and bioerodable are used interchangeably and refer to zinc alloys that are capable of being completely degraded and/or eroded into different degrees of molecular levels when exposed to bodily fluids, such as blood, and can be gradually resorbed, absorbed, and/or eliminated by the body.

As compared to conventional adult coronary stents, implanted stent substrates formed from bioresorbable zinc alloys described herein can have a size in a crimped state small enough to allow for introduction into a vascular introducer sheath to allow for delivery in infants and small children. For these applications the stents can be crimpable onto about 4 mm to about 12 mm balloons and still fit into about 1 to about 2 mm (e.g., 4-6 French) delivery sheaths. This requires the bioresorbable zinc alloy to be extruded into small diameter rods and drawn into thin-walled tubes, which can be laser cut into the desired stent pattern. Advantageously, the bioresorbable zinc alloy can be heated and annealed without developing mechanical stress cracks, fractures before laser cutting. The wall thickness of the stent substrate can be, for example, about 80 μm to about 160 μm in order to have a small enough crossing profile to allow the stent to be crimped and fit in the delivery sheath.

The implantable stent substrate can be radially expanded from a first geometric shape capable of fitting in the 1 to 2 mm delivery sheath to a second geometric shape having an outer diameter of, for example, about 4 mm to about 12 mm. Advantageously, a stent substrate, which is radially expandable to about 4 mm to about 12 mm that is formed using the bioresorbable zinc alloy described herein can be used pediatric and adult conditions in which large bioresorbable stents would be beneficial. Such conditions can include, for example, infant/pediatric pulmonary artery stenosis (e.g., about 4 to about 12 mm), infant/pediatric aortic coarctation (e.g., about 4 to about 12 mm), neonatal patent ductus arteriosus stenting (e.g., about 6 to about 8 mm), infant RVOT stenting (e.g., about 4 to about 8 mm), pulmonary vein stenosis/occlusion (e.g., about 4 to about 10 mm), adult peripheral artery disease (about 4 to about 12 mm), adult coronary artery disease (e.g., about 4 to about 5 mm), adult carotid artery disease (e.g., about 6 to about 10 mm), adult renal artery stenosis (e.g., about 4 to about 10 mm), and adult and children venous and arterial thrombosis recanalization (e.g., about 4 to about 12 mm). It will be appreciated that the bioresorbable stent substrates can be used in any type of bodily lumen including the coronary artery, superficial femoral artery, popliteal artery, neural vessels, and the sinuses.

In general, treatments employing the endoluminal prosthesis described herein require the stent substrate to provide mechanical support to a vessel for a period of time and then desirably to absorb away and disappear from the implant site. The important properties of a bioresorbable stent or scaffolding include mechanical and degradation properties. The mechanical requirements include high radial strength, high radial stiffness, and high fracture toughness. The degradation properties include the absorption profile, for example, the change in elemental make-up, radial strength, and mass with time. Specific aspects of the absorption profile include the time that the stent maintains radial strength before starting to decrease and the total absorption time (complete mass loss from implant site).

A stent scaffolding made from a bioresorbable zinc alloy described herein may be designed to maintain its radial strength and/or radial stiffness once implanted to provide mechanical support to the vessel for a prescribed time period and maintain patency of the lumen. The radial strength must be sufficiently high initially to support the lumen at a desired diameter. The period of time that the scaffold is required or desired to maintain patency depends on the type of treatment. After this time period, the vessel is healed sufficiently to maintain an expanded diameter without support. Therefore, after this time period, the scaffolding may start to lose radial strength and/or radial stiffness due to compositional degradation. As the scaffolding degrades further, it starts to lose mechanical integrity and then experiences mass loss and eventually absorbs away completely or there are negligible traces left behind.

The optimal degradation time for a bioresorbable stent is dependent on the indication for use and the target lesion characteristics. For congenital heart lesions, such as coarctation of the aorta and branch pulmonary artery stenosis, it is desirable to maintain the radial force through 6 months. Congenital heart lesions can be treated with stents much different than stents used for coronary artery disease. It is likely that congenital target lesions will need to be treated with a stent more than one time. The major reason for this is that the stent will be placed in a growing vessel. The rate of somatic growth is highest in the first 2 years of life. A vessel with a stent placed in it at 6 months of life will grow significantly over the next 6 months. As such, the stent and target lesion may not have complete remodeling by the time the stent is losing radial strength. Therefore, the old stent and target lesion may need to be re-stented with a larger new zinc alloy bioresorbable stent in order to match the size of the surrounding vessel both proximal and distal to the stented area.

In some embodiments, the zinc alloy bioresorbable stent that can maintain radial strength through at least 6 months in order to meet the demands of pediatric applications. Furthermore, the stent can have the capacity to be modified by increasing strut thickness or coating it with a material that could slow down the degradation rate if necessary.

In some embodiments, it is desired that once the stent support is no longer needed by the lumen, the bioresorbable scaffold should be resorbed as fast as possible while also meeting all basic safety requirements during its degradation period. Such safety requirements can include a gradual disintegration and resorption that does not allow release of fragments that could cause adverse events such as thrombosis. In this way, the stent scaffold enables the vessel healing as well as enabling the advantages mentioned herein of a bioresorbable scaffold to the greatest extent. It is desirable for a bioresorbable scaffold to have an absorption time of about 6 to 24 months for coronary vascular application, about eighteen months (e.g., 8-20 months) for a peripheral application (e.g., superficial femoral artery (SFA)) and/or politeal artery), 18-24 months for neural applications, and less than a year for nasal applications.

In some embodiments, the implantable stent substrate after implantation in vasculature of a subject in need thereof, can maintain ductility after exposure to vascular pulsability and during degradation as well as maintain vessel patency at least 6 months.

With respect to radial strength and stiffness, a stent should have sufficient radial strength and/or stiffness to withstand structural loads, namely radial compressive forces, imposed on the stent so that the stent can supports the walls of a vessel at a selected diameter for a desired time period. A bioresorbable stent with adequate radial strength and/or stiffness enables the stent to maintain a lumen at a desired diameter for a sufficient period of time after implantation into a vessel.

In addition, the stent should possess sufficient toughness or resistance to fracture to allow for crimping, expansion, and cyclic loading without fracture or cracking that would compromise the function of the stent. The toughness or resistance to fracture can be characterized for a material by the elongation at break and for a stent by the number and degree of cracks in a scaffold during use, such as after crimping or deployment. These aspects of the use of the stent involve deformation of various hinge portions of the structural elements of the scaffold. To achieve this goal, a stent must have optimal ductility and tensile strength. Stents formed from the bioresorbable zinc alloy described herein can have excellent elongation to failure (>25%) and tensile strength (>250 MPa) allowing for therapeutic maintenance of vessel patency at the target size while being delivered through small introducer sheaths. For example, the implantable stent substrate can have a radial strength of at least about 2 N/mm at an outer diameter of about 6 mm and a radial strength of at least about 0.9 N/mm at outer diameter of 10 mm.

In some embodiments, the bioresorbable zinc alloy includes, consists essentially, or consists of at least four alloying elements selected from the group consisting of silver (Ag) in an amount of about 1.0 wt. % to about 6.0 wt. %, manganese (Mn) in an amount of about 0.1 wt. to about 2.0 wt. %, zirconium (Zr) in an amount of about 0.05 wt. % to about 1.0 wt. %, copper (Cu) in an amount of about 0.5 wt. % to about 1.2 wt. %, and optionally titanium (Ti) in an amount of 0 to about 0.4 wt. %, with the balance of the alloy being zinc and incidental impurities, based on the total weight of the zinc alloy. The incidental purities can include other elements at amounts less than about 0.01 wt. %, about 0.001 wt. %, about 0.0001 wt. %, or less.

In some embodiments, the zinc alloy can include Ag in an amount of about 1.0 wt. % to about 6.0 wt. %, about 1.5 wt. % to about 5.5 wt. %, about 2.0 wt. % to about 5.0 wt. %, about 2.5 wt. % to about 4.5 wt. %, about 3.0 wt. % to about 4.0 wt. %, about 1.0 wt. % to about 2.0 wt. %, about 1.0 wt. % to about 3.0 wt. %, about 1.0 wt. % to about 4.0 wt. %, about 1.0 wt. % to about 5.0 wt. %, about 2.0 wt. % to about 6.0 wt. %, about 3.0 wt. % to about 6.0 wt. %, about 4.0 wt. % to about 6.0 wt. %, or about 5.0 wt. % to about 6.0 wt. %.

In other embodiments, the zinc alloy can include Mn in an amount of about 0.1 wt. % to about 2.0 wt. %, about 0.2 wt. % to about 1.8 wt. %, about 0.4 wt. % to about 1.6 wt. %, about 0.6 wt. % to about 1.0 wt. %, about 0.8 wt. % to about 1.2 wt. %, about 0.1 wt. % to about 1.0 wt. %, about 0.1 wt. % to about 0.8 wt. %, about 0.1 wt. % to about 0.6 wt. %, about 0.1 wt. % to about 0.4 wt. %, about 1.0 wt. % to about 2.0 wt. %, about 1.2 wt. % to about 2.0 wt. %, about 1.4 wt. % to about 2.0 wt. %, or about 1.6 wt. % to about 2.0 wt. %.

In other embodiments, the zinc alloy can include Zr in an amount of about 0.05 wt. % to about 1.0 wt. %, about 0.10 wt. % to about 0.90 wt. %, about 0.20 wt. % to about 0.80 wt. %, about 0.40 wt. % to about 0.60 wt. %, about 0.05 wt. % to about 0.50 wt. %, about 0.05 wt. % to about 0.40 wt. %, about 0.05 wt. % to about 0.30 wt. %, about 0.1 wt. % to about 0.3 wt. %, about 0.5 wt. % to about 1.0 wt. %, about 0.60 wt. % to about 1.0 wt. %, about 0.70 wt. % to about 1.0 wt. %, or about 0.80 wt. % to about 1.0 wt. %.

In other embodiments, the zinc alloy can include Cu in an amount of about 0.1 wt. % to about 2.0 wt. %, about 0.2 wt. % to about 1.8 wt. %, about 0.4 wt. % to about 1.6 wt. %, about 0.5 wt. % to about 1.2 wt. %, about 0.8 wt. % to about 1.2 wt. %, about 0.1 wt. % to about 1.0 wt. %, about 0.1 wt. % to about 0.8 wt. %, about 0.1 wt. % to about 0.6 wt. %, about 0.1 wt. % to about 0.4 wt. %, about 1.0 wt. % to about 2.0 wt. %, about 1.2 wt. % to about 2.0 wt. %, about 1.4 wt. % to about 2.0 wt. %, or about 1.6 wt. % to about 2.0 wt. %.

In other embodiments, the zinc alloy can optionally include Ti in an amount of 0 to about 0.50 wt. %, about 0.05 wt. % to about 0.45 wt. %, about 0.05 wt. % to about 0.4 wt. %, about 0.05 wt. % to about 0.35 wt. %, about 0.05 wt. % to about 0.30 wt. %, about 0.05 wt. % to about 0.25 wt. %, about 0.05 wt. % to about 0.20 wt. %, about 0.05 wt. % to about 0.15 wt. %, about 0.01 wt. % to about 0.10 wt. %, about 0.02 wt. % to about 0.10 wt. %, or about 0.03 wt. % to about 0.10 wt. %.

In still other embodiments, the bioresorbable zinc alloy includes, consists essentially, or consists of about 2.0 wt. % to about 5.0 wt. % Ag, about 0.4 wt. % to about 1.0 wt. % Mn, about 0.5 wt. % to about 1.2 wt. % Cu, about 0.1 wt. % to about 0.3% wt. % Zr, and 0 to about 0.4 wt. % titanium (Ti), the balance being Zn and incidental elements and impurities. For example, the bioresorbable zinc alloy can include, consist essentially of, or consist of about 4 wt. % Ag, about 0.8 wt. % Cu, about 0.6 wt. % Mn, and about 0.15 wt. % Zr, with the balance of the alloy being zinc and incidental impurities, based on the total weight of the zinc alloy. The incidental purities can include other elements at amounts less than about 0.01 wt. %, about 0.001 wt. %, about 0.0001 wt. %, or less.

Advantageously, the bioresorbable zinc alloy used to form the implantable stent substrate can have an ultimate tensile strength of greater than about 250 MPa and/or an elongation to failure greater than about 25%, which can allow for therapeutic maintenance of vessel patency at the target size while being delivered through small introducer sheaths.

In other embodiments, the bioresorbable zinc alloy can have substantially uniform microstructure with a Zn grain size of about 0.1 μm to about 10 μm and a plurality of uniformly distributed intermetallic particles at the grain boundaries. The intermetallic particles have a size about 100 nm to about 1 μm and comprise Ag, Mn, and/or Zr particles and/or combinations of Ag, Mn, and/or Zr alone or in combination with Zn.

An implantable stent substrate can formed from the bioresorbable zinc alloy by casting the zinc alloy, extruding the cast zinc alloy to form tubes, drawing the extruded tubes, laser cutting the stent shape, and optionally electropolishing the stent.

In some embodiments, the bioresorbable zinc alloy can be cast at a temperature of about 650° C. into ingots having a cylindrical shape with a nominal diameter of about 28 mm and a length of about 100 mm. The cast ingots of bioresorbable zinc alloy can be machined and homogenized or annealed at a high temperature and for a time effective grain size, precipitate size/fraction and crystallographic texture of the zinc alloy. For example, the cast and machined ingot can be homogenized for 24 hours at a temperature of about 400°

C. The cast, machined, and homogenized ingot can then be extruded at a temperature in the range of about 250° C. to about 300° C., at an extrusion ratio of about 8:1 to about 40:1, and at an extrusion speed of about 2 mm/min to about 10 mm/min to form a round rod with a diameter of about 4 mm. Follow formation of the rods of the bioresorbable zinc alloy, the rods can be warm tube extruded, drawn, laser cut to the desired stent pattern, and optionally electropolished to form the implantable stent substrate.

In other embodiments, the implantable stent substrate can include a coating on the implantable stent substrate. The coating can inhibit degradation of the stent substrate and optionally hold or release at least one therapeutic agent immediately and/or over a sustained duration after implantation of the endoluminal prosthesis.

The coating can include, for example, a biodegradable polymer that is coated on the implantable stent substrate. Examples of biodegradable polymers for use in embodiments described herein, include, but are not limited to: poly(a-hydroxy acids), such as, polycapro lactone (PCL), poly(lactide-co-glycolide) (PLGA), polylactide (PLA), and polyglycolide (PGA), and combinations and blends thereof, PLGA-PEG (polyethylene glycol), PLA-PEG, PLA-PEG-PLA, polyanhydrides, trimethylene carbonates, polyorthoesters, polyaspirins, polyphosphagenes, and tyrozine polycarbonates Any therapeutic agent (or "drug") may be incorporated into, coated on, or otherwise attached to the stent or coating, in various embodiments. Examples of such therapeutic agents include, but are not limited to, anti-thrombotics, anticoagulants, antiplatelet agents, anti-lipid agents, thrombolytics, anti-proliferatives, anti-inflammatories, agents that inhibit hyperplasia, smooth muscle cell inhibitors, antibiotics, growth factor inhibitors, cell adhesion inhibitors, cell adhesion promoters, anti-mitotics, anti-fibrins, antioxidants, anti-neoplastics, agents that promote endothelial cell recovery, matrix metalloproteinase inhibitors, anti-metabolites, anti-allergic substances, viral vectors, nucleic acids, monoclonal antibodies, inhibitors of tyrosine kinase antisense compounds, oligio-nucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan.

Examples of anti-thrombotics, anticoagulants, antiplatelet agents, and thrombolytics include, but are not limited to, sodium heparin, low molecular weight heparins, heparinoids, hirudin, argatroban, forskolin, vapriprost, prostacyclin and prostacylin analogues, dextran, Dphe-pro-arg-chloromethylketone (synthetic anti-thrombin), dipyridamole, glycoprotein IIb/IIIa (platelet membrane receptor antagonist antibody), recombinant hirudin, thrombin inhibitors, and thrombolytic agents.

Examples of cytostatic or anti-proliferative agents include, but are not limited to, rapamycin and its analogs, including everolimus, zotarolimus, tacrolimus and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of anti-neoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, and antibiotics, such as doxorubicin hydrochloride and mitomycin. Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:
1. An endoluminal prosthesis comprising:
    an implantable stent and/or scaffold substrate which is convertible from a compressed first tubular geometric shape to a radially dilated dimensionally stable second tubular geometric shape, the stent and/or scaffold substrate comprising a bioresorbable zinc alloy, the zinc alloy including at least four alloying elements selected from the group consisting of silver (Ag) in an amount of about 1.0 wt. % to about 6.0 wt. %, manganese (Mn) in an amount of about 0.1 wt. to about 2.0 wt. %, zirconium (Zr) in an amount of about 0.05 wt. % to about 1.0 wt. %, copper (Cu) in an amount of about 0.5 wt. % to about 1.2 wt. %, and titanium (Ti) in an amount of 0 to about 0.4 wt. %, with the balance of the alloy being zinc and incidental impurities at amounts less than about 0.01 wt. %, wherein the zinc alloy has substantially uniform microstructure with a Zn grain size of about 0.1 μm to about 10 μm and a plurality of uniformly distributed intermetallic particles at the grain boundaries.

2. The endoluminal prosthesis of claim 1, wherein the zinc alloy has an ultimate tensile strength of greater than about 250 MPa.

3. The endoluminal prosthesis of claim 1, wherein the zinc alloy has an elongation to failure greater than about 25%.

4. The endoluminal prosthesis of claim 1, wherein the intermetallic particles have a size about 100 nm to about 1 μm.

5. The endoluminal prosthesis of claim 1, wherein the implantable scaffold and/or stent substrate is configured to maintain ductility after exposure to vascular pulsability and during degradation when implanted in vasculature.

6. The endoluminal prosthesis of claim 1, upon implantation in the vasculature of a subject in need thereof, the endoluminal prosthesis is configured to maintain vessel patency for at least 6 months.

7. The endoluminal prosthesis of claim 1, the zinc alloy being cast at a temperature of about 650° C. and extruded at a temperature in the range of about 250° C. to about 300° C.

8. The endoluminal prosthesis of claim 7, the zinc alloy being extruded at an extrusion ratio of about 8:1 to about 40:1.

9. The endoluminal prosthesis of claim 1, wherein the second tubular geometric shape of the implantable stent and/or scaffold substrate has an outer diameter of about 4 mm to about 12 mm.

10. The endoluminal prosthesis of claim 1, wherein the implantable stent and/or scaffold substrate has a radial strength of at least about 2 N/mm at a first outer diameter of about 6 mm and a radial strength of at least about 0.9 N/mm at a second outer diameter of about 10 mm.

11. The endoluminal prosthesis of claim 1, further comprising a coating on the implantable stent and/or scaffold substrate.

12. The endoluminal prosthesis of claim 11, wherein the coating holds or releases at least one therapeutic agent.

13. A scaffold and/or stent with a tubular framework structure of interconnected stent struts fabricated from a bioresorbable zinc alloy, the tubular framework being convertible from a compressed first geometric shape into a radially dilated, dimensionally stable, tubular second geometric shape, the bioresorbable zinc alloy the zinc alloy including at least four alloying elements selected from the group consisting of silver (Ag) in an amount of about 1.0 wt. % to about 6.0 wt. %, manganese (Mn) in an amount of about 0.1 wt. to about 2.0 wt. %, zirconium (Zr) in an amount of about 0.05 wt. % to about 1.0 wt. %, copper (Cu) in an amount of about 0.5 wt. % to about 1.2 wt. %, and titanium (Ti) in an amount of 0 to about 0.4 wt. %, with the balance of the alloy being zinc and incidental impurities at amounts less than about 0.01 wt. %, wherein the zinc alloy has substantially uniform microstructure with a Zn grain size of about 0.1 μm to about 10 μm and a plurality of uniformly distributed intermetallic particles at the grain boundaries.

14. The scaffold and/or stent of claim 13, wherein the zinc alloy has an ultimate tensile strength of greater than about 250 MPa.

15. The scaffold and/or stent of claim 13, wherein the zinc alloy has an elongation to fatigue greater than about 25%.

16. The scaffold and/or stent of claim 13, wherein the intermetallic particles have a size about 100 nm to about 1 μm.

17. The scaffold and/or stent of claim 13, wherein the scaffold and/or stent has a radial strength of at least about 2 N/mm at a first outer diameter of about 6 mm and a radial strength of at least about 0.9 N/mm at a second outer diameter of about 10 mm.

18. The scaffold and/or stent of claim 13, wherein the second tubular geometric shape is sized for treating at least one of infant/pediatric pulmonary artery stenosis, infant/pediatric aortic coarctation, neonatal patent ductus arteriosus stenting, infant RVOT stenting, pulmonary vein stenosis/occlusion, adult peripheral artery disease, adult coronary artery disease, adult carotid artery disease, adult renal artery stenosis, or adult and children venous and arterial thrombosis recanalization.

* * * * *